United States Patent
Szarski

(10) Patent No.: US 10,497,110 B2
(45) Date of Patent: Dec. 3, 2019

(54) IDENTIFYING A PATHWAY FOR CONDITION OF ASSEMBLY VALIDATION

(71) Applicant: The Boeing Company, Chicago, IL (US)

(72) Inventor: Martin Szarski, Canterbury (AU)

(73) Assignee: The Boeing Company, Chicago, IL (US)

( * ) Notice: Subject to any disclaimer, the term of this patent is extended or adjusted under 35 U.S.C. 154(b) by 235 days.

(21) Appl. No.: 15/441,104

(22) Filed: Feb. 23, 2017

(65) Prior Publication Data
US 2018/0240227 A1    Aug. 23, 2018

(51) Int. Cl.
*G06T 7/00* (2017.01)
*G06T 7/38* (2017.01)
(Continued)

(52) U.S. Cl.
CPC ............... *G06T 7/001* (2013.01); *B64F 5/60* (2017.01); *G06T 7/0006* (2013.01); *G06T 7/344* (2017.01);
(Continued)

(58) Field of Classification Search
CPC ..... B64F 5/10; B64F 5/60; G01N 2021/8883; G01N 21/8851; G01N 2201/0216;
(Continued)

(56) References Cited

U.S. PATENT DOCUMENTS

2008/0310754 A1    12/2008  Safai et al.
2015/0012171 A1*    1/2015  Richter ................... G06T 7/001
                                                    701/32.9
(Continued)

FOREIGN PATENT DOCUMENTS

EP    2937756    10/2015
EP    3045394    7/2016
(Continued)

OTHER PUBLICATIONS

Miljković, Zoran et al., "New hybrid vision-based control approach for automated guided vehicles", The International Journal of Advanced Manufacturing Technology, Jul. 6, 2012, pp. 231-549, vol. 66, No. 1-4, Springer, London, XP055484685.

*Primary Examiner* — Jessica M Prince
(74) *Attorney, Agent, or Firm* — Haynes and Boone, LLP

(57) ABSTRACT

A method and apparatus for establishing a pathway for performing an automated validation of a condition of assembly. A sensor system coupled to an automated guided vehicle is moved into test positions relative to the structure. Image data is generated at each test position, using the sensor system, to build test images. Each test image is registered to a computer model of the structure to form registered images that are added to a collection of registered images. An optimal set of positions that will allow an entirety of an area of interest to be captured using a fewest number of registered images from the collection of registered images is determined. A pathway is generated for moving the automated guided vehicle to each optimal position in a least amount of time. A computer file identifying the pathway is generated for use in performing the automated validation of the condition of assembly.

20 Claims, 13 Drawing Sheets

(51) Int. Cl.
  *G06T 7/33* (2017.01)
  *G06T 7/73* (2017.01)
  *H04N 7/18* (2006.01)
  *B64F 5/60* (2017.01)
(52) U.S. Cl.
  CPC .......... *G06T 7/38* (2017.01); *G06T 7/74* (2017.01); *H04N 7/185* (2013.01); *G01N 2201/0216* (2013.01); *G01N 2201/10* (2013.01); *G06T 2207/30108* (2013.01); *G06T 2207/30248* (2013.01)
(58) Field of Classification Search
  CPC .......... G01N 2201/10; G05B 19/41895; G05B 2219/45066; G05D 1/0246; G05D 2201/0207; G06Q 10/04; G06Q 50/04; G06T 2207/30108; G06T 2207/30248; G06T 7/0006; G06T 7/001; G06T 7/344; G06T 7/38; G06T 7/74; H04N 7/185; Y02P 90/285; Y02P 90/60
  See application file for complete search history.

(56) References Cited

U.S. PATENT DOCUMENTS

| | | | |
|---|---|---|---|
| 2016/0033251 A1* | 2/2016 | Pinkston | G01B 21/00 702/81 |
| 2016/0075020 A1* | 3/2016 | Szarski | B25J 9/1664 700/160 |
| 2016/0116905 A1* | 4/2016 | Szarski | G05B 19/4099 700/187 |
| 2016/0264262 A1 | 9/2016 | Colin et al. | |

FOREIGN PATENT DOCUMENTS

| | | |
|---|---|---|
| FR | 2945630 | 11/2010 |
| WO | WO 2014/145471 | 9/2014 |

* cited by examiner

IDENTIFYING A PATHWAY FOR CONDITION OF ASSEMBLY VALIDATION

CROSS REFERENCE TO RELATED APPLICATION

This application is related to U.S. patent application Ser. No. 15/441,082, entitled "Automated Validation of Condition of Assembly," filed Feb. 23, 2017, which is hereby incorporated by reference in its entirety.

BACKGROUND

1. Field

The present disclosure relates to manufacturing and, more particularly, to performing an automated validation of a condition of assembly for a structure.

2. Background

Assembling a structure that is comprised of hundreds of thousands of parts may be a complex process that involves multiple stages of assembly. Accordingly, validating a condition of assembly over the course of these stages of assembly helps ensure quality control. A "condition of assembly" for a structure may be, for example, the degree to which a current build of the structure matches or conforms to a design specification for that structure. As one example, the assembly of an aircraft structure, such as a fuselage, may be a complex multi-stage process. Validating the condition of assembly of the fuselage, for example, after a particular stage of assembly may include determining whether the current build of the fuselage is within selected tolerances.

Currently, validating the condition of assembly of a complex structure, such as a fuselage, is typically performed manually. For example, a human operator may manually inspect a fuselage and compare the build of the fuselage to hundreds of printed engineering drawings of the fuselage, a computer aided design (CAD) model of the fuselage, or both. In some cases, this type of validation may require the operator to have special training and experience to maneuver through the drawings or model of the fuselage. Further, this type of evaluation may be more time-consuming and more prone to error than desired. Therefore, it would be desirable to have improved methods and systems for validating the condition of assembly for structures.

SUMMARY

In one illustrative embodiment, a method is provided for establishing a pathway for performing an automated validation of a condition of assembly for a structure. A sensor system coupled to an automated guided vehicle may be moved into a plurality of test positions relative to the structure. Image data may be generated at each test position of the plurality of test positions, using the sensor system, to build a plurality of test images. Each test image of the plurality of test images may be registered to a computer model of the structure to form a plurality of registered images that are added to a collection of registered images. An optimal set of positions that will allow an entirety of an area of the structure that is of interest to be captured using a fewest number of registered images from the collection of registered images, is determined from the plurality of test positions. A pathway is generated for moving the automated guided vehicle to each of the optimal set of positions in a least amount of time. A computer file is generated for use in performing an automated validation process to validate the condition of assembly for the structure in which the computer file identifies the pathway.

In another illustrative embodiment, a method for establishing a pathway for performing an automated validation of a condition of assembly for a fuselage structure is provided. A sensor system coupled to an automated guided vehicle may be moved into a plurality of test positions through the fuselage structure. Image data may be generated at each test position of the plurality of test positions, using the sensor system, to build a plurality of test images. Each test image of the plurality of test images generated may be registered to a computer model of the fuselage structure. An optimal set of positions that will allow an entirety of an area of the fuselage structure that is of interest to be captured using a fewest number of test images is determined from the plurality of test positions. A pathway is generated for moving the automated guided vehicle to each of the optimal set of positions in a least amount of time. A file is generated for use in performing an automated validation process to validate the condition of assembly for the fuselage structure in which the file identifies the pathway.

In yet another illustrative embodiment, an apparatus comprises a processor that comprises a registration component and an optimizing component. The registration component receives a plurality of test images from a sensor system that generated the plurality of test images at a plurality of test positions relative to a structure. The registration component registers each test image of the plurality of test images generated to a computer model of the structure. The optimizing component determines an optimal set of positions from the plurality of test positions that allows an entirety of an area of the structure that is of interest to be captured using a fewest number of test images. The optimizing component generates a pathway for moving the automated guided vehicle to each of the optimal set of positions in a least amount of time. The optimizing component generates a file for use in performing the automated validation of the condition of assembly for the structure in which the file identifies the pathway.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
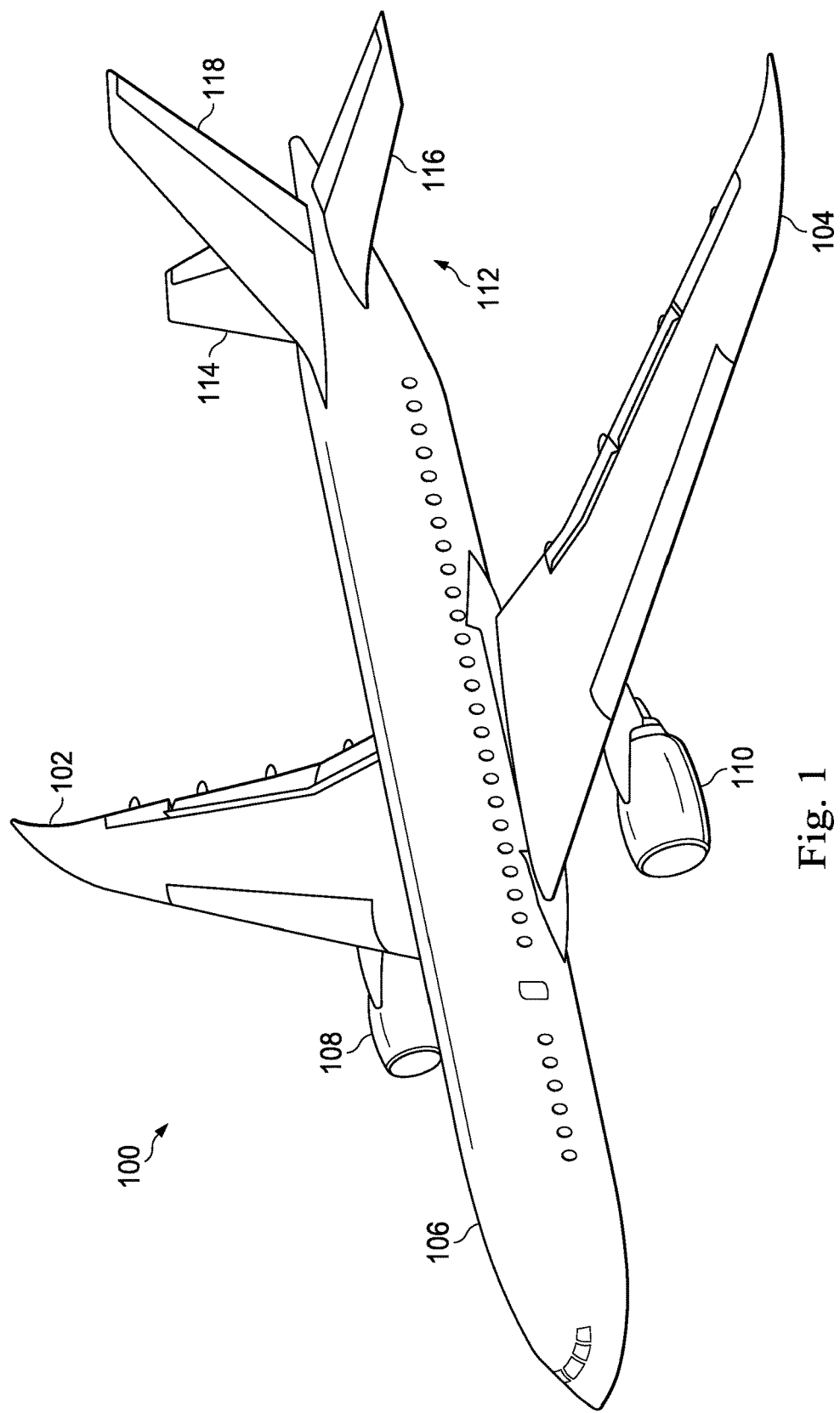
FIG. 1 is an illustration of an aircraft in accordance with an illustrative embodiment.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances well known methods, procedures, components, and circuits have not been described in detail so as not to unnecessarily obscure aspects of the embodiments.

The illustrative embodiments recognize and take into account that automating the validation of the condition of assembly for a structure may allow this validation to be performed more quickly and accurately as compared to manual methods. Further, by automating the condition of assembly validation, the downtime needed for this validation process may be reduced. As one illustrative example, when the validation is to be performed between two stages of assembly, the validation process may reduce the downtime needed before the next stage of assembly can begin.

Additionally, the illustrative embodiments provide a method and apparatus for automating the validation of a condition of assembly for a structure in a manner that limits the time and processing resources needed to perform this validation.

In one illustrative embodiment, a plurality of images of a structure may be generated using a sensor system. The structure may be, for example, a fuselage. Validating the condition of assembly for the fuselage may involve, for example, without limitation, confirming the presence of tens of thousands to hundreds of thousands of fasteners in specific locations. Each image generated may capture tens, hundreds, or thousands of fasteners.

The plurality of images of the fuselage may be registered to a computer model of the structure. Each image in the plurality of images may be segmented based on registration of the plurality of images to the computer model to form a plurality of image sections. A score may be generated for the condition of assembly of the fuselage based on whether each image section in the plurality of image sections meets a corresponding condition. The score may indicate whether the condition of assembly is valid.

In some embodiments, the sensor system that generates the plurality of images may be coupled to an automated guided vehicle. The automated guided vehicle may be moved along a predetermined path relative to the structure to allow the sensor system to generate the plurality of images. In particular, the automated guide vehicle may be moved along the predetermined path such that the sensor system may be moved into an optimal set of positions that enable an entirety of an area of the structure that is of interest to be captured using the fewest number of images. In this manner, the time and processing resources needed to perform the automated validation of the condition of assembly may be reduced. The illustrative embodiments may provide a computerized method and apparatus for efficiently identifying the optimal set of positions out of a plurality of test positions. The plurality of test positions may include, for example, without limitation, hundreds, thousands, or tens of thousands of test positions.

Referring now to the figures, in these illustrative examples, the same reference numeral may be used in more than one figure. This reuse of a reference numeral in different figures represents the same element in the different figures.

FIG. 1 is an illustration of an aircraft, depicted in accordance with an illustrative embodiment. Aircraft 100 includes wing 102 and wing 104 attached to fuselage 106. Aircraft 100 includes engine 108 attached to wing 102 and engine 110 attached to wing 104. Aircraft 100 also includes tail section 112. Horizontal stabilizer 114, horizontal stabilizer 116, and vertical stabilizer 118 are attached to tail section 112.

Aircraft 100 is an example of an aircraft manufactured using methods and systems for automated validation of condition of assembly in accordance with the illustrative embodiments described below. For example, without limitation, fuselage 106 may be an example of one implementation of a structure built using a multi-stage process with automated validation of condition of assembly performed after at least one stage of assembly.

Figure 2:
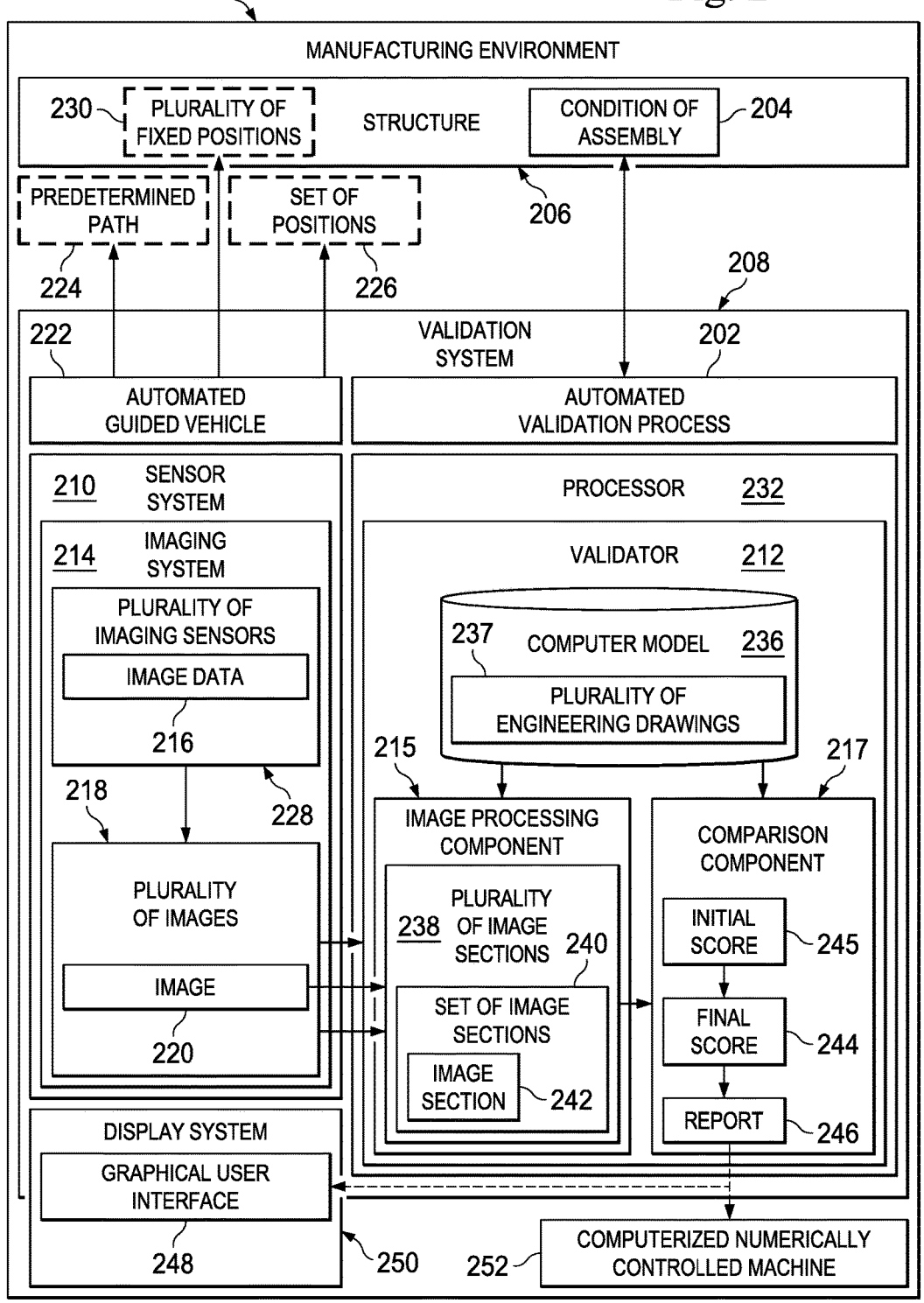
FIG. 2 is a block diagram of a manufacturing environment in accordance with an illustrative embodiment.

FIG. 2 is a block diagram of a manufacturing environment depicted in accordance with an illustrative embodiment. Manufacturing environment 200 is an example of an environment in which automated validation process 202 may be performed. Automated validation process 202 may be an automated process by which condition of assembly 204 for structure 206 may be evaluated and determined to be either valid or invalid. In particular, automated validation process 202 may enable condition of assembly 204 for structure 206 to be evaluated with zero or minimal involvement of human operators. Condition of assembly 204 for structure 206 may be, for example, the degree to which a current build of structure 206 matches or conforms to a design specification for structure 206.

Depending on the implementation, structure 206 may take a number of different forms. In one illustrative example, structure 206 takes the form of a fuselage structure that is being assembled to form fuselage 106 of aircraft 100 in FIG. 1. In other illustrative examples, structure 206 may be a different type of aircraft structure, such as wing 102, wing 104, or tail section 112 of aircraft 100 in FIG. 1. In still other illustrative examples, structure 206 may be a spacecraft structure, a watercraft structure, a sub-assembly for a ground vehicle, or some other type of structure that is built using a multi-stage assembly process.

Validation system 208 may be used to perform automated validation process 202. In one illustrative example, validation system 208 may be used to perform automated validation process 202 after a particular stage of assembly has been completed. This stage of assembly may include, for example, without limitation, the drilling of thousands to tens of thousands of holes in structure 206 and the installation of thousands to tens of thousands fasteners within these holes.

In this illustrative example, validation system 208 includes sensor system 210 and validator 212. Sensor system 210 and validator 212 may be communicatively coupled. For example, sensor system 210 and validator 212 may be configured to communicate using one or more wired communications links, one or more wireless communications links, one or more optical communications links, or a combination thereof.

In this illustrative embodiment, sensor system 210 takes may take the form of imaging system 214. Imaging system 214 may include one or more cameras configured to generate image data 216 for use in generating plurality of images 218 of structure 206. An image of plurality of images 218, such as image 220, may capture a portion of structure 206. This portion of structure 206 may be a large section of structure 206. For example, without limitation, when structure 206 takes the form of a fuselage structure, image 220 may capture a section of a fuselage panel, an entire fuselage panel, multiple fuselage panels, a flooring, or some other portion of the fuselage structure.

In one illustrative example, imaging system 214 may be coupled to automated guided vehicle 222. For example, without limitation, imaging system 214 may be removably attached to automated guided vehicle 222, permanently affixed to automated guided vehicle 222, built-in as part of automated guided vehicle 222, or coupled to automated guided vehicle 222 in some other manner.

Automated guided vehicle 222 may be moved along predetermined path 224 relative to structure 206 to allow sensor system 210 to generate image data 216 at set of positions 226 relative to structure 206. Set of positions 226 may be an optimal set of positions selected for allowing an entirety of an area of structure 206 that is of interest to be captured using the fewest number of images. Moving automated guided vehicle 222 relative to structure 206 may include moving automated guided vehicle 222 within an interior of structure 206, along an exterior of structure 206, along a platform located at a selected distance from structure 206, along a flooring at a selected distance from structure 206, along a track system relative to structure 206, in some other suitable manner, or a combination thereof.

In other illustrative examples, imaging system 214 may comprise plurality of imaging sensors 228 that are positioned in plurality of fixed positions 230 relative to structure 206. Plurality of fixed positions 230 may be an optimal plurality of positions selected for allowing an entirety of an area of structure 206 that is of interest to be captured using the fewest number of images and the fewest number of imaging sensors.

Sensor system 210 may send plurality of images 218 to validator 212 for processing. Depending on the implementation, validator 212 may be implemented using software, hardware, firmware, or a combination thereof. When software is used, the operations performed by validator 212 may be implemented using, for example, without limitation, program code configured to run on a processor unit. When firmware is used, the operations performed by validator 212 may be implemented using, for example, without limitation, program code and data stored in persistent memory to run on a processor unit.

When hardware is employed, the hardware may include one or more circuits that operate to perform the operations performed by validator 212. Depending on the implementation, the hardware may take the form of a circuit system, an integrated circuit, an application specific integrated circuit (ASIC), a programmable logic device, some other suitable type of hardware device configured to perform any number of operations, or a combination thereof.

In one illustrative example, validator 212 takes the form of processor 232. In some illustrative examples, validator 212 may be a computer system that comprises a single computer or multiple computers in communication with each other. In one illustrative example, validator 212 may include image processing component 215 and comparison component 217.

Upon receiving plurality of images 218 from sensor system 210, validator 212 registers plurality of images 218 to computer model 236 of structure 206. Computer model 236 may be, for example, a computer aided design model of structure 206. In other illustrative examples, computer model 236 may comprise plurality of digital engineering drawings 237 of structure 206.

Validator 212 segments each of plurality of images 218 based on the registration of plurality of images 218 to computer model 236 to form plurality of image sections 238. In particular, each image in plurality of images 218 may be segmented to form a set of image sections, such as set of image sections 240, that is added to plurality of image sections 238.

As one illustrative example, image 220 may be segmented to create set of image sections 240 based on the registration of image 220 to computer model 236. For example, based on the registration of image 220 to computer model 236, validator 212 may identify each location in image 220 at which a single feature of interest is expected to be seen. Validator 212 may segment image 220 to create an image section for each one of these locations. In this manner, each image section in set of image sections 240 captures a portion of structure 206 that is expected to have a single feature of interest.

Image section 242 may be an example of one of set of image sections 240. Image section 242 may be expected to capture a feature of interest selected from one of, for example, without limitation, a hole, a fastener installed in a hole, an absence of a hole, an absence of a fastener, or some other type of feature. Image section 242 may be segmented from image 220 by being, for example, without limitation, snipped, cropped, or otherwise extracted from image 220.

Depending on the implementation, set of image sections 240 formed from image 220 may make up the entirety of image 220 or only a portion of image 220. For example, without limitation, in some cases, only the portions of image 220 expected to have features of interest may be snipped, cropped, or otherwise extracted from image 220.

In some illustrative examples, the receiving of plurality of images 218 from sensor system 210, the registration of plurality of images 218 to computer model 236, and the segmenting of each image of plurality of images 218 may be performed by image processing component 215 of validator 212. In some cases, only the registration and segmenting steps may be performed by image processing component 215.

Once plurality of image sections 238 has been created, validator 212 may generate final score 244 for condition of assembly 204. Validator 212 may generate final score 244 based on whether each image section in plurality of image sections 238 meets a corresponding condition. In some cases, comparison component 217 of validator 212 may perform a comparison of plurality of image sections 238 to computer model 236 to generate final score 244.

For example, without limitation, validator 212 may generate initial score 245 by computing the percentage of image sections in plurality of image sections 238 that meet the corresponding condition for each respective image section. The corresponding condition used to evaluate each image section may be determined based on the corresponding portion of computer model 236 to which each image section, such as image section 242, is registered. For example, the corresponding condition for a particular image section may be the presence or absence of a particular feature of interest, as specified by computer model 236. The feature of interest may be, for example, without limitation, a hole or a fastener that has been installed in a hole.

As one illustrative example, validator 212 may compare image section 242 to the corresponding portion of computer model 236 to which image section 242 is registered. This corresponding portion of computer model 236 may indicate that the corresponding condition to be met is the presence of a fastener. Validator 212 may use one or more image recognition techniques to determine whether or not image section 242 includes a fastener.

In other illustrative examples, all image sections in plurality of image sections 238 may be evaluated based on the same corresponding condition. For example, the corresponding condition may be the presence of a fastener. In this example, initial score 245 may be the percentage of image sections in plurality of image sections 238 that include a fastener.

In some illustrative examples, validator 212 uses initial core 245 as final score 244 for condition of assembly 204. Final score 244 may indicate that condition of assembly 204 is valid when final score 244 is above a selected threshold. The selected threshold may be, for example, without limitation, 84 percent, 88 percent, 92 percent, 95 percent, 97 percent, or some other percentage, depending on the implementation.

In other illustrative examples, validator 212 may make adjustments to initial score 245 based on whether one or more invalidating events have occurred to generate final score 244. For example, based on the portion of computer model 236 to which image section 242 is registered and the importance of the corresponding condition, the failure of image section 242 to meet this corresponding condition may be considered an invalidating event. When an invalidating event occurs, validator 212 may adjust initial score 245 accordingly.

In some cases, a single invalidating event may cause validator 212 to adjust initial score 245 to 0 percent. Thus, a single invalidating event may cause condition of assembly 204 to be invalid despite initial score 245 being above the selected threshold. In other instances, each invalidating event may cause validator 212 to reduce initial score 245 by a selected amount. Some invalidating events may be weighted as more important than other invalidating events. For example, validator 212 may be configured to reduce initial score 245 by a greater amount based on the occurrence of one type of invalidating event as compared to another type of invalidating event. In still other illustrative examples, validator 212 may use initial score 245 as final score 244 but may generate an alert or flag when one or more invalidating events have occurred.

Validator 212 may create report 246 that includes final score 244, as well as any alerts or flags that have been generated. In one illustrative example, validator 212 displays report 246 on graphical user interface 248 on display system 250. Display system 250 may be communicatively coupled to validator 212. In other illustrative examples, validator 212 may display only final score 244 and any alerts or flags that have been generated on graphical user interface 248. Display system 250 may be part of validations system 208 or independent of validation system 208, depending on the implementation.

In some illustrative examples, validator 212 sends report 246 to computerized numerically controlled machine 252 for processing. Report 246 may be used to adjust the programming for computerized numerically controlled machine 252 or generate a command for computerized numerically controlled machine 252. As one illustrative example, computerized numerically controlled machine 252 may run a program that initiates a next stage of assembly when computerized numerically controlled machine 252 receives report 246 indicating that condition of assembly 204 for structure 206 is valid.

In this manner, validation system 208 allows automated validation process 202 to be performed efficiently. This automated validation process 202 may reduce the downtime in between stages of assembly. Further, using validation system 208 to validate condition of assembly 204 of structure 206 may improve the accuracy with which condition of assembly 204 is evaluated.

Figure 3:
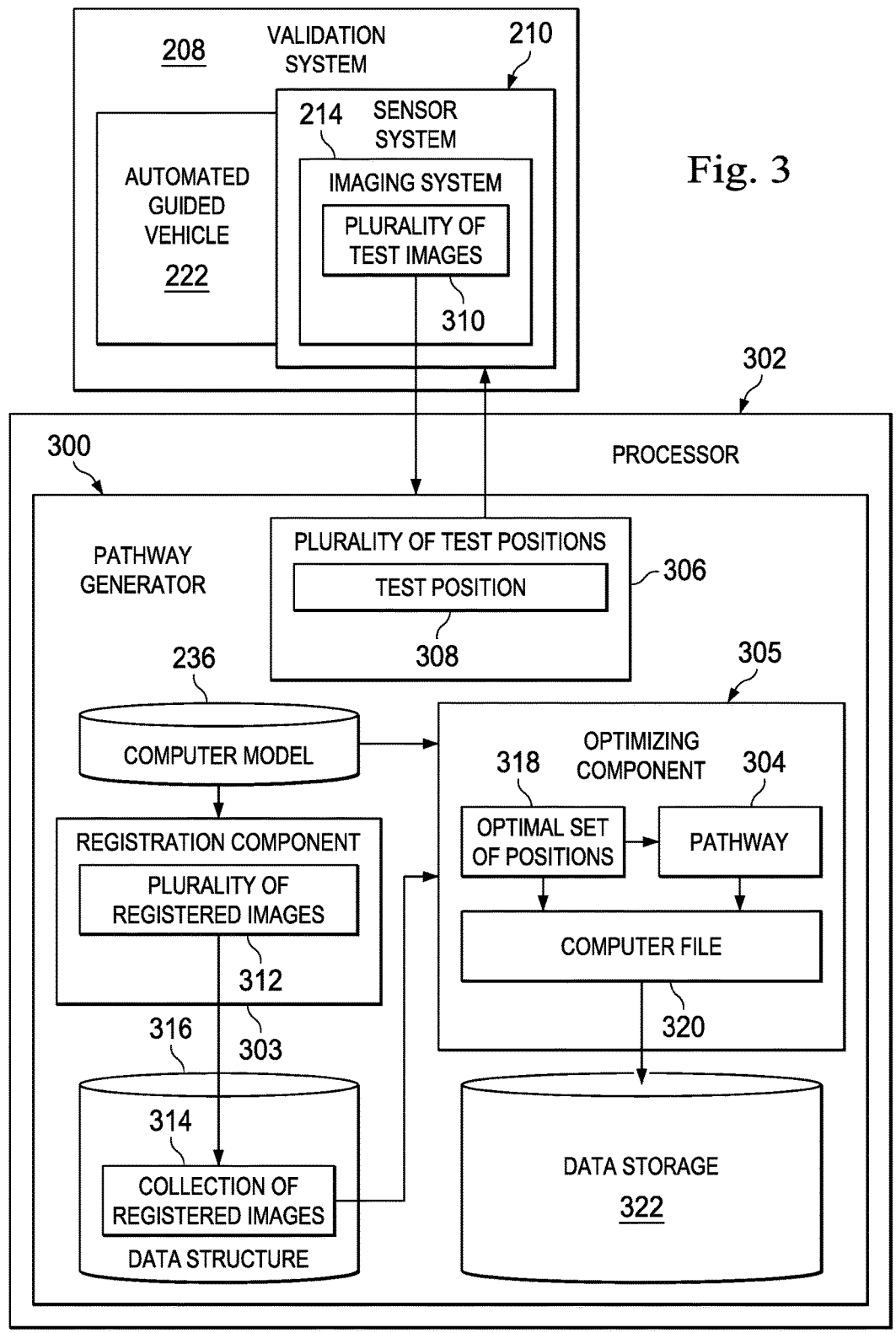
FIG. 3 is a block diagram of a pathway generator and a sensor system in accordance with an illustrative embodiment.

FIG. 3 is a block diagram of a pathway generator and sensor system 210 from FIG. 2, depicted in accordance with an illustrative embodiment. In this illustrative example, pathway generator 300 is implemented as part of validator 212 in FIG. 2.

In other illustrative examples, pathway generator 300 may be implemented independently of validator 212. For example, pathway generator 300 may be implemented in processor 302 within validation system 208. Processor 302 may be communicatively coupled to processor 232 in FIG. 2. Further, processor 302 may be communicatively coupled to sensor system 210. In still other illustrative examples, pathway generator 300 may be implemented independently of validation system 208.

Pathway generator 300 is used to establish pathway 304 for performing automated validation process 202 in FIG. 2. Pathway 304 may be used as the predetermined path 224 in FIG. 2. In one illustrative example, pathway generator 300 includes registration component 303 and optimizing component 305.

In this illustrative example, sensor system 210 is coupled to automated guided vehicle 222. Sensor system 210 is moved into plurality of test positions 306 relative to structure 206. Plurality of test positions 306 may include, for example, without limitation, tens, hundreds, thousands, or tens of thousands of test positions, depending on the implementation. In one illustrative example, plurality of test positions 306 may include between 100 and 100,000 test positions. Test position 308 is an example of one of plurality of test positions 306. Test position 308 may comprise a location, an orientation, or both for sensor system 210. Accordingly, test position 308 defines a unique field of view for sensor system 210 relative to structure 206. Sensor system 210 generates image data at each test position of plurality of test positions 306 to build plurality of test images 310. Sensor system 210 then sends plurality of test images 310 to pathway generator 300 for processing.

Pathway generator 300 registers each test image of plurality of test images 310 to computer model 236 of structure 206 to form plurality of registered images 312. In particular, registration component 303 of pathway generator 300 may register each test image of plurality of test images 310 to computer model 236. Plurality of registered images 312 are added to collection of registered images 314. In this illustrative example, collection of registered images 314 may be stored in data structure 316. Data structure 316 may take the form of, for example, without limitation, a database, a data repository, associative memory, or some other type of data structure.

Pathway generator 300 determines which positions from plurality of test positions 306 will allow an entirety of an area of structure 206 that is of interest to be captured using the fewest number of registered images from collection of registered images 314. The particular positions identified form optimal set of positions 318. Optimal set of positions 318 may be used as set of positions 226 in FIG. 2. In one illustrative example, these above described steps in the identification of optimal set of positions 318 may be performed by optimizing component 305 of pathway generator 300.

In this illustrative example, pathway generator 300 uses optimal set of positions 318 to establish pathway 304 for moving automated guided vehicle 222 relative to structure 206 to perform automated validation process 202. For example, without limitation, pathway generator 300 may compute pathway 304 for moving automated guided vehicle 222 relative to structure 206 such that sensor system 210 may be moved into optimal set of positions 318 in a least amount of time. In some cases, the generation of pathway 304 is performed by optimizing component 305.

Pathway generator 300 then generates computer file 320 that identifies pathway 304 for automated guided vehicle 222 and optimal set of positions 318 for sensor system 210. In one illustrative example, the computer file 320 may be generated by optimizing component 305.

In some illustrative examples, pathway generator 300 may send computer file 320 to validator 212 in FIG. 2 for use in performing automated validation process 202 to validate condition of assembly 204 for structure 206. In other illustrative examples, pathway generator 300 may store computer file 320 in data storage 322. Data storage 322 may take the form of memory in communication with processor 302, cloud storage, or some other type of data storage.

In these examples, computer file 320 may be retrieved by validator 212 from data storage 322 for use in performing automated validation process 202. Using pathway 304 and optimal set of positions 318 identified in computer file 320 as predetermined path 224 for performing the automated validation process 202 may reduce the time and amount of processing resources needed to perform automated validation process 202.

Pathway 304 and optimal set of positions 318 identified in computer file 320 may be used for performing automated validation process 202 for other structures. For example, validator 212 may retrieve computer file 320 for performing automated validation process 202 for a plurality of structures (not shown) that are being assembled based on computer model 236. In other words, pathway 304 and optimal set of positions may be used to perform automated validation process 202 for other structures that match a same design specification as structure 206.

The illustrations of manufacturing environment 200 in FIG. 2, validation system 208 in FIG. 2, and pathway generator 300 in FIG. 3 are not meant to imply physical or architectural limitations to the manner in which an illustrative embodiment may be implemented. Other components in addition to or in place of the ones illustrated may be used. Some components may be optional. Additionally, the blocks may be presented to illustrate functional components. One or more of these blocks may be combined, divided, or combined and divided into different blocks when implemented in an illustrative embodiment.

For example, when automated guided vehicle 222 is moved through structure 206 in the form of a fuselage, such as fuselage 106 in FIG. 1, automated guided vehicle 222 may be moved within the interior cylindrical portions of the fuselage. However, in other illustrative examples, when structure 206 takes the form of wing 102 in FIG. 1, automated guided vehicle 222 may be moved along the exterior surface of wing 102. In this manner, automated guided vehicle 222 may be moved in different ways relative to structure 206 depending on the type of structure 206.

Figure 4:
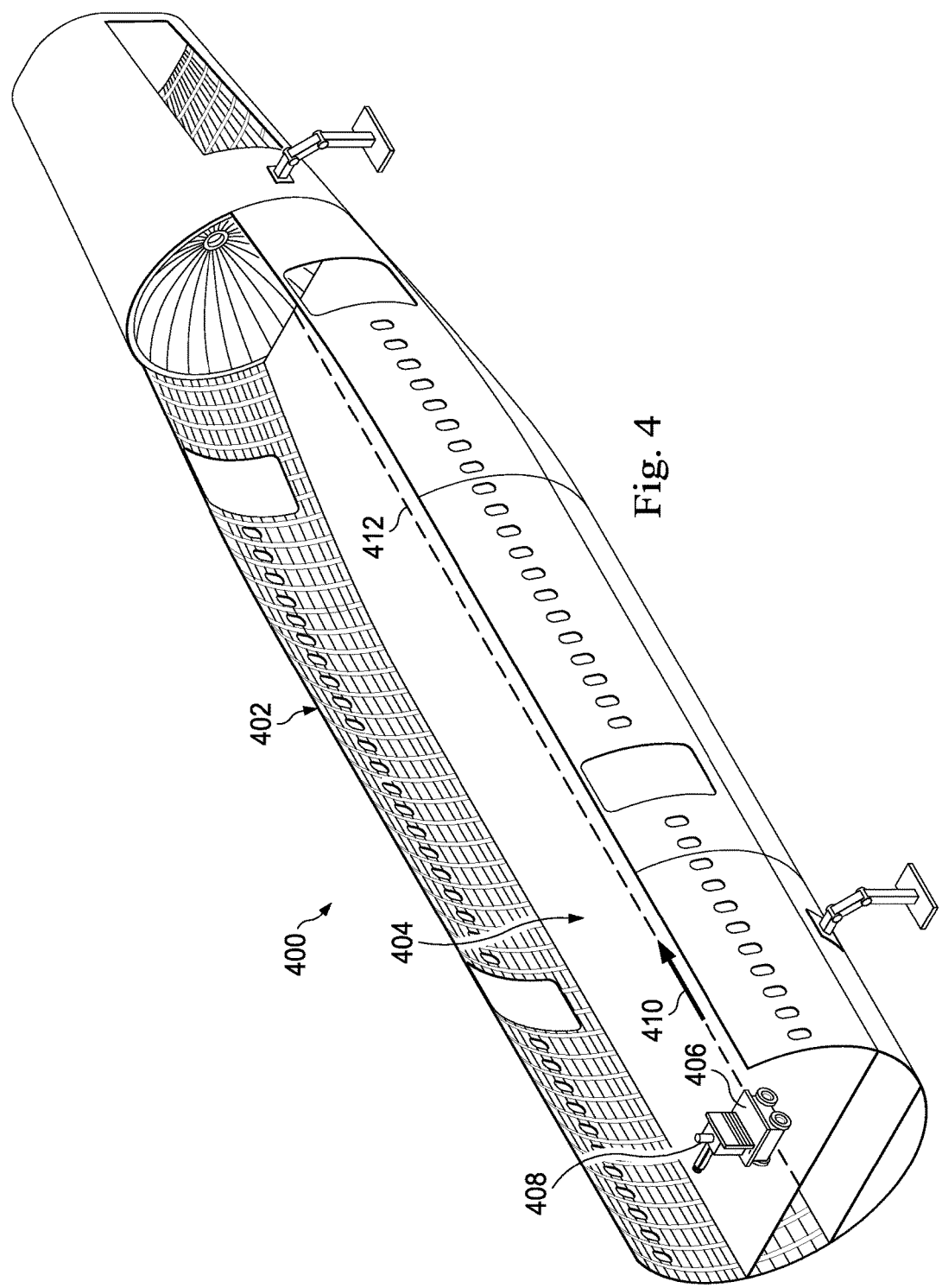
FIG. 4 is an isometric view of a fuselage structure in accordance with an illustrative embodiment.

FIG. 4 is an isometric view of a fuselage structure, depicted in accordance with an illustrative embodiment. Fuselage structure 400 may be an example of one implementation for structure 206 described in FIG. 2. Further, fuselage structure 400 may be in the middle of an assembly process for building a fuselage, such as fuselage 106 in FIG. 1.

Fuselage structure 400 includes plurality of fuselage panels 402. In this illustrative example, fuselage structure 400 may have top fuselage panels that are not shown such that interior 404 of fuselage structure 400 may be better seen.

Automated guided vehicle 406 may move through interior 404 of fuselage structure 400 to perform various operations using imaging system 408 attached to automated guided vehicle 406. Imaging system 408 may be an example of one implementation for imaging system 214 in FIG. 2. In one illustrative example, imaging system 408 may be controlled to change orientation relative to fuselage structure 400 such that imaging system 408 can capture different view of interior 404.

Depending on the implementation, imaging system 408 may have one or more degrees of linear freedom, one or more degrees of rotational freedom, or a combination thereof relative to automated guided vehicle 406. Accordingly, imaging system 408 may have six degrees of freedom, three degrees of freedom, one degree of freedom, or some other number of degrees of freedom relative to automated guided vehicle 406. For example, without limitation, imaging system 408 may be capable of moving with three rotational degrees of freedom relative to automated guided vehicle 406.

In one illustrative example, automated guided vehicle 406 may be moved through interior 404 of fuselage structure 400 for the purpose of establishing a pathway, such as pathway 304 in FIG. 3, for performing automated validation process 202 described in FIG. 2. For example, without limitation, automated guided vehicle 406 may be moved along predetermined test pathway 410 relative to fuselage structure 400. In this illustrative example, predetermined test pathway 410 may be a straight-line path along centerline 412 of fuselage structure 400. In other illustrative examples, predetermined test pathway 410 may be a curved pathway, a zig-zag pathway, or some other type of pathway.

Further, automated guided vehicle 406 may be moved to various positions along predetermined test pathway 410 to allow imaging system 408 to be moved into a plurality of test positions. For example, without limitation, automated guided vehicle 406 may be moved to about 50 positions along predetermined test pathway 410. At each of these 50 positions, imaging system 408 may be moved relative to automated guided vehicle 406 into some number of test positions. For example, without limitation, imaging system 408 may be moved into 10 or more test positions at each stop made by automated guided vehicle 406 along predetermined test pathway 410. Each test position may comprise a test location and a test orientation relative to a reference coordinate system. This reference coordinate system may be a coordinate system for automated guided vehicle 406, a coordinate system for fuselage structure 400, or some other of coordinate system.

At each test position, imaging system 408 generates a test image. The plurality of test images generated by imaging system 408 may be sent to, for example, pathway generator 300 described in FIG. 3 for processing. Pathway generator 300 may use these test images to establish pathway 304 for performing automated validation process 202 for fuselage structure 400. Once pathway 304 has been established, pathway 304 may be used to perform automated validation process 202 for fuselage structure 400, as well as other fuselage structures being assembled according to a same design specification as fuselage structure 400.

Figure 5:
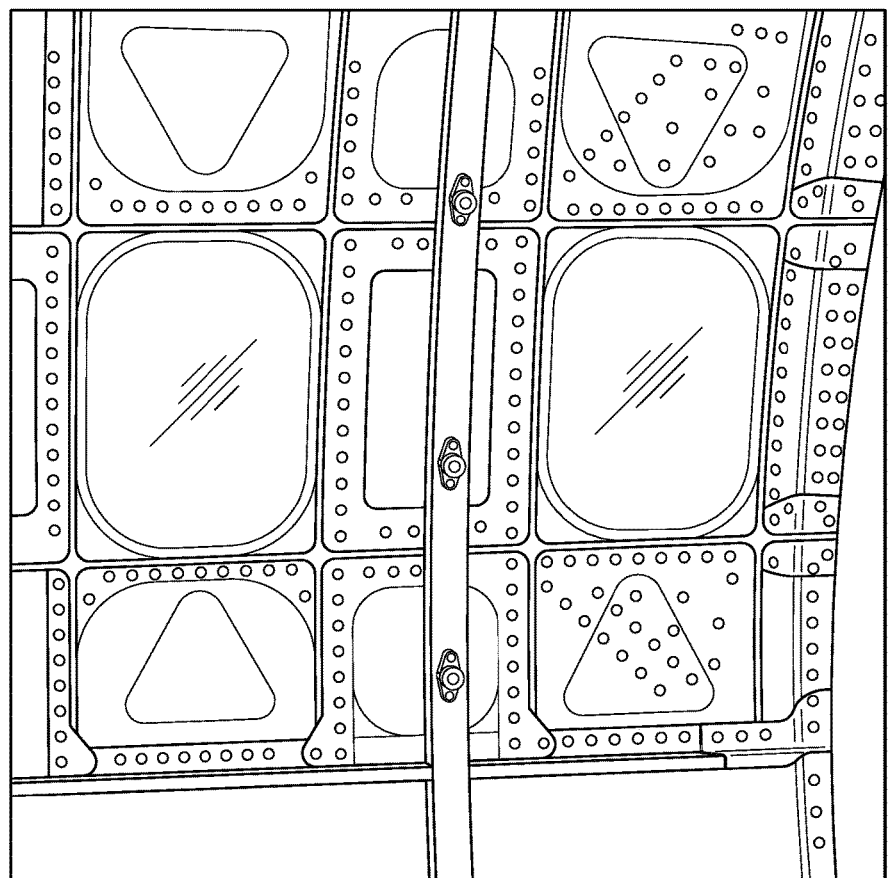
FIG. 5 is an illustration of an image of a portion of a fuselage structure in accordance with an illustrative embodiment.
Figure 5:
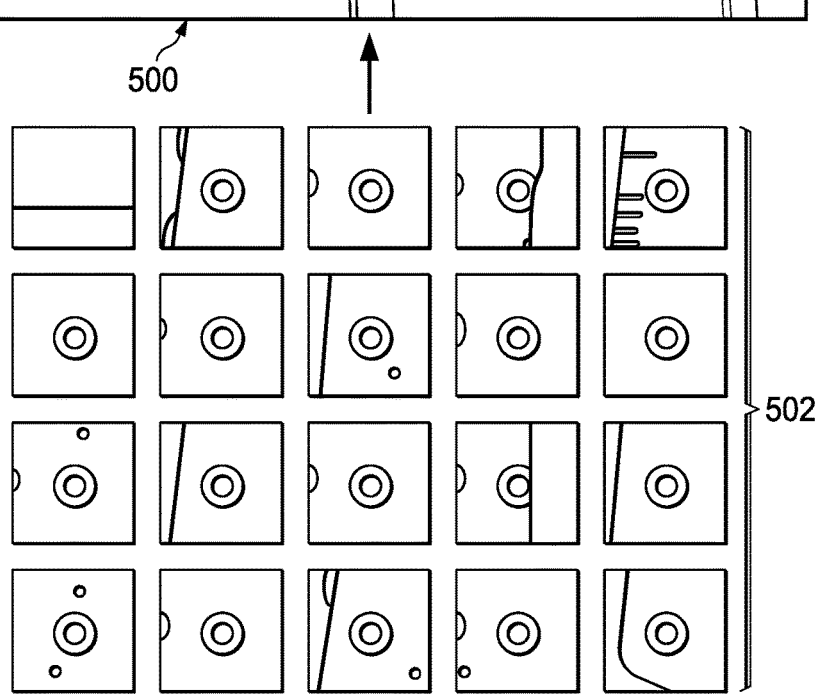

FIG. 5 is an illustration of an image of a portion of fuselage structure 400 from FIGS. 4-5, depicted in accordance with an illustrative embodiment. Image 500 may be an example of one implementation for image 220 described in FIG. 2. Image 500 may be generated by, for example, imaging system 408 in FIG. 4 within interior 404 of fuselage structure 400.

Validator 212 from FIG. 2 may register image 500 to a computer model for fuselage structure 400. Based on this registration, validator 212 may identify the various portions of image 500 that are expected to have fasteners installed. Validator 212 may then segment image 500 into set of image sections 502. For example, without limitation, validator 212 may snip, crop, or otherwise extract plurality of image sections 502 from image 500. Set of image sections 502 may be an example of one implementation, for set of image sections 240 described in FIG. 2.

Each image section of plurality of image sections 502 may then be analyzed to determine whether that image section meets a corresponding condition based on the computer model for fuselage structure 400. For example, without limitation, the corresponding condition may be either a presence of a fastener or the absence of a fastener.

Figure 6:
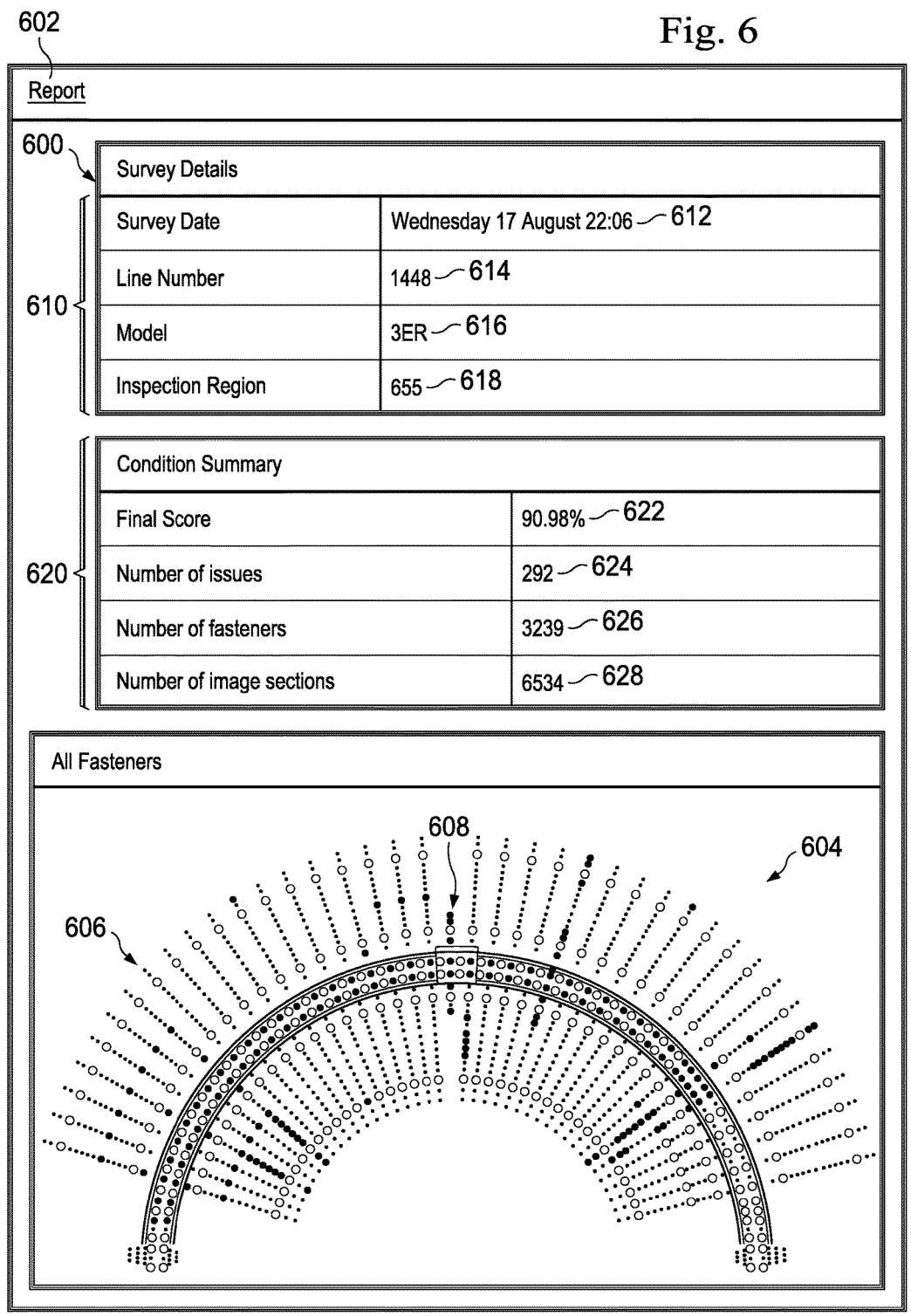
FIG. 6 is an illustration of a report displayed on a graphical user interface in accordance with an illustrative embodiment.

FIG. 6 is an illustration of a report displayed on a graphical user interface, depicted in accordance with an illustrative embodiment. Report 600 is displayed on graphical user interface 602. Report 600 may be an example of one implementation for report 246 in FIG. 2. Graphical user interface 602 may be an example of one implementation for graphical user interface 248 in FIG. 2. Report 600 may be generated by validator 212 in FIG. 2 after an automated validation of condition of assembly for fuselage structure 400 in FIG. 4 has been performed.

As depicted, report 600 includes diagram 604. Diagram 604 may represent interior 404 of fuselage structure 400. In this illustrative example, diagram 604 identifies plurality of expected fasteners 606, which may be all of the fasteners that are expected to be present in fuselage structure 400 after a particular stage of assembly.

In this illustrative example, set of graphical indicators 608 may be used to indicate each fastener of plurality of expected fasteners 606 that is not present in fuselage structure 400. In this manner, diagram 604 may allow a human operator viewing report 600 to easily and readily identify the locations on fuselage structure 400 that may require further attention.

Further, report 600 also includes general information 610. For example, without limitation, general information 610 may include date 612, line number 614, model 616, and inspection region 618. Date 612 may identify the date on which the automated validation of the condition of assembly was performed. Line number 614 and model 616 may specifically identify fuselage structure 400. Inspection region 618 may identify the particular region of fuselage structure 400 for which the automated validation of the condition of assembly was performed.

Additionally, report 600 includes condition summary 620. Condition summary 620 may identify the results of the automated validation of the condition of assembly. For example, without limitation, condition summary 620 may identify final score 622, number of issues 624, number of fasteners 626, and number of image sections 628. Final score 622 may be an example of one implementation for final score 244 in FIG. 2.

Final score 622 identifies the percentage of image sections analyzed that met their respective corresponding conditions. Number of issues 624 identifies the number of issues that were detected. In other words, number of issues 624 may identify the number of image sections that did not meet their respective corresponding conditions. Number of fasteners 626 identifies the number of fasteners that were recognized by validator 212 using one or more image techniques. Number of image sections 628 may identify the total number of image sections that were used and analyzed to generate report 600.

The illustrations in FIG. 1 and FIGS. 4-6 are not meant to imply physical or architectural limitations to the manner in which an illustrative embodiment may be implemented. Other components in addition to or in place of the ones illustrated may be used. Some components may be optional. The different components shown in FIG. 1 and FIGS. 4-6 may be illustrative examples of how components shown in block form in FIGS. 2 and 3 can be implemented as physical structures. Additionally, some of the components in FIG. 1 and FIGS. 4-6 may be combined with components in FIGS. 2 and 3, used with components in FIGS. 2 and 3, otherwise involved with components in FIGS. 2 and 3, or a combination thereof.

Figure 7:
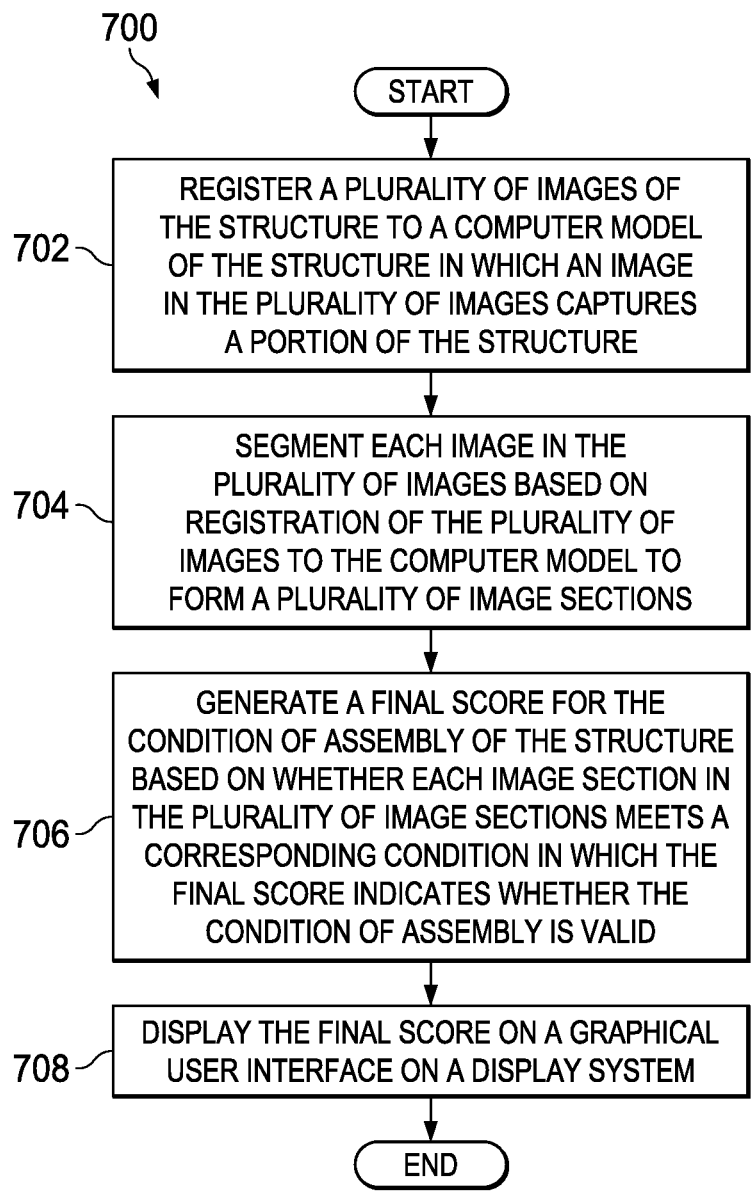
FIG. 7 is an illustration of a method for performing an automated validation of a condition of assembly for a structure in accordance with an illustrative embodiment.

FIG. 7 is an illustration of a method for performing an automated validation of a condition of assembly for a structure, depicted in accordance with an illustrative embodiment. The method 700 illustrated in FIG. 7 may be used to perform, for example, automated validation process 202 as previously described in FIG. 2. The method 700 is illustrated as a set of operations or processes. Not all of the illustrated operations may be performed in all embodiments of method 700. Additionally, one or more processes that are not expressly illustrated in FIG. 7 may be included before, after, in between, or as part of the operations. In some embodiments, one or more of the operations may be optional and therefore omitted.

The method 700 may begin by registering a plurality of images of the structure to a computer model of the structure in which an image in the plurality of images captures a portion of the structure (operation 702). In operation 702, the structure may be, for example, a fuselage structure such as fuselage structure 400 in FIG. 4. In other illustrative examples, the structure may be some other type of aircraft structure. Next, each image in the plurality of images may be segmented based on registration of the plurality of images to the computer model to form a plurality of image sections (operation 704). Operation 704 may be performed using, for example, without limitation, one or more image recognition and registration techniques.

Thereafter, a final score for the condition of assembly of the structure may be generated based on whether each image section in the plurality of image sections meets a corresponding condition in which the final score indicates whether the condition of assembly is valid (operation 706). In one illustrative example, the final score may be the percentage of the plurality of image sections that met their respective corresponding condition based on their registration to the computer model. The final score may then be displayed on a graphical user interface on a display system (operation 708), with the process terminating thereafter. Each of the operations of the automated validation process described in the method 700 in FIG. 7 may be performed autonomously.

Figure 8:
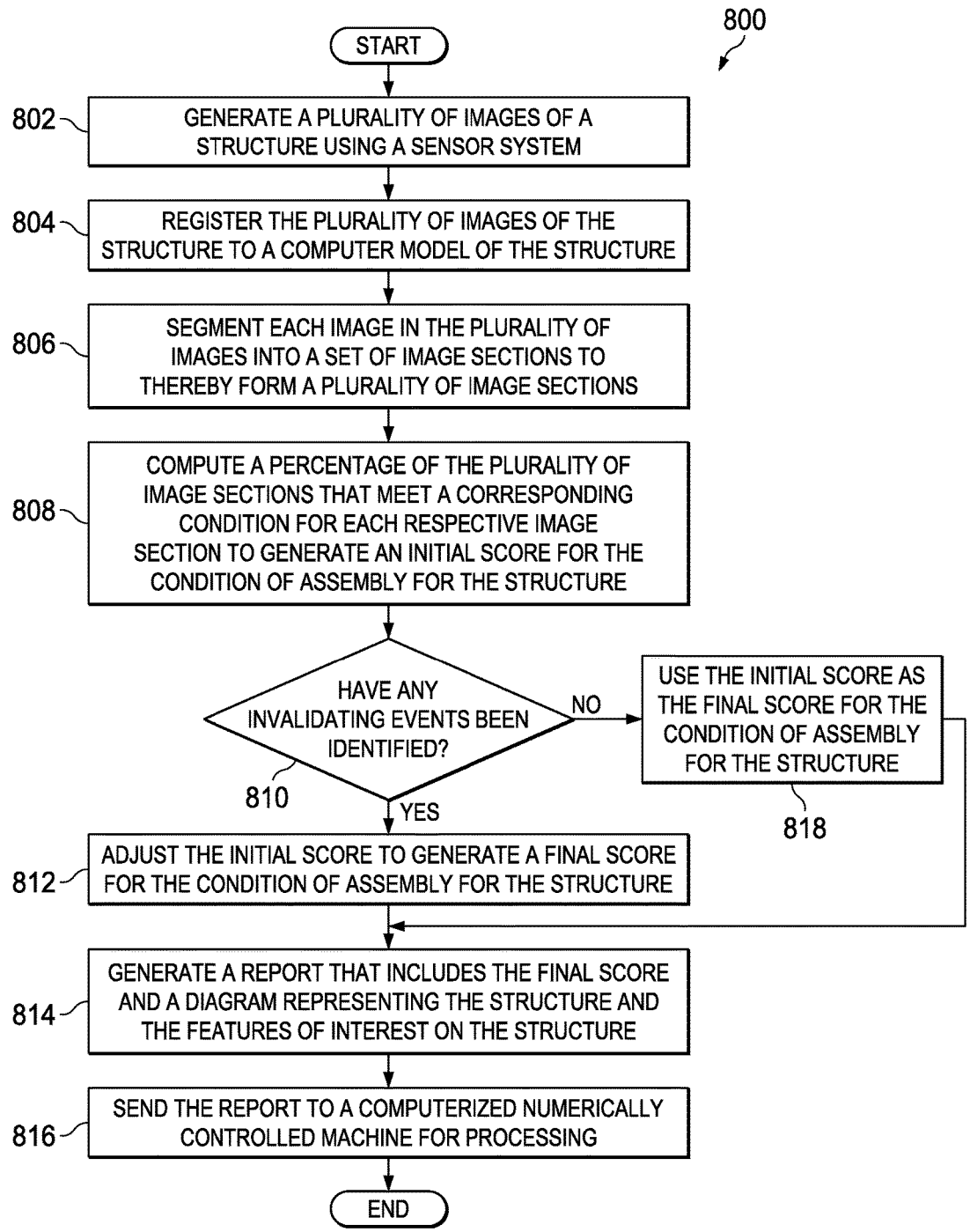
FIG. 8 is an illustration of a method for performing an automated validation of a condition of assembly for a structure in accordance with an illustrative embodiment.

FIG. 8 is an illustration of a method for performing an automated validation of a condition of assembly for a structure, depicted in accordance with an illustrative embodiment. The method 800 illustrated in FIG. 8 may be used to perform, for example, automated validation process 202 as previously described in FIG. 2. The method 800 is illustrated as a set of operations or processes. Not all of the illustrated operations may be performed in all embodiments of method 800. Additionally, one or more processes that are not expressly illustrated in FIG. 8 may be included before, after, in between, or as part of the operations. In some embodiments, one or more of the operations may be optional and therefore omitted.

The method 800 may begin by generating a plurality of images of a structure using a sensor system (operation 802). In one illustrative example, the sensor system comprises a plurality of sensors positioned at a plurality of fixed positions relative to the structure. In other illustrative examples, the sensor system may be coupled to an automated guided vehicle. In these examples, the automated guided vehicle may be moved along a predetermined path relative to the structure to move the sensor system into a set of positions to generate the plurality of images. The set of positions may be an optimal set of positions that allow an entirety of an area or region of the structure that is of interest to be captured with the fewest number of images.

Next, the plurality of images of the structure may be registered to a computer model of the structure (operation 804). In operation 804, the computer model may be, for example, without limitation, a computer aided design model. Then, each image in the plurality of images is segmented into a set of image sections to thereby form a plurality of image sections (operation 806). Operation 806 may be performed by, for example, without limitation, cropping, snipping, or otherwise extracting one or more image sections from each image. In some cases, the entirety of the image may be segmented. In other cases, only certain portions of the image may be segmented such that each image section created captures a portion of the structure that is expected to have a single feature of interest. The single feature of interest may be, for example, without limitation, a hole, a fastener installed in the hole, or some other type of feature that can be visually detected.

Thereafter, a percentage of the plurality of image sections that meet a corresponding condition for each respective image section is computed to generate an initial score for the condition of assembly for the structure (operation 808). In operation 808, a corresponding condition for a particular image section may be, for example, either a presence or absence of a particular feature of interest. In some illustrative examples, the corresponding condition may be selected from one of a presence of a hole, a presence of a fastener installed in a hole, an absence of a hole, an absence of a fastener in a hole, or some other type of condition.

A determination may be made as to whether any invalidating events have been identified (operation 810). In operation 810, an invalidating event may be, for example, a particular image section not meeting a corresponding condition that is critical to the condition of assembly for the structure. For example, in some cases, the presence of fastener in a particular location may be critical to the condition of assembly. If any invalidating events have been identified, the initial score is adjusted to generate a final score for the condition of assembly for the structure (operation 812). In particular, in operation 812, the initial score is adjusted based on the invalidating events identified. Operation 812 may be performed by, for example, adjusting the initial score to zero percent to indicate that the invalidating events have made the condition of assembly invalid. In other illustrative examples, an adjustment may be made to the initial score for each invalidating event, with the adjustment being weighted based on an importance of each invalidating event to the condition of assembly for the structure.

A report that includes the final score and a diagram representing the structure and the features of interest on the structure is then generated (operation 814). The report is sent to a computerized numerically controlled machine for processing (operation 816), with the process terminating thereafter. In some cases, the report is used to adjust the computerized numerically controlled machine or generate a command for the computerized numerically controlled machine.

With reference again to operation 810, if no invalidating events have been identified, the initial score is used as the final score for the condition of assembly for the structure (operation 818). The method 800 then proceeds to process 814 as described above.

Figure 9:
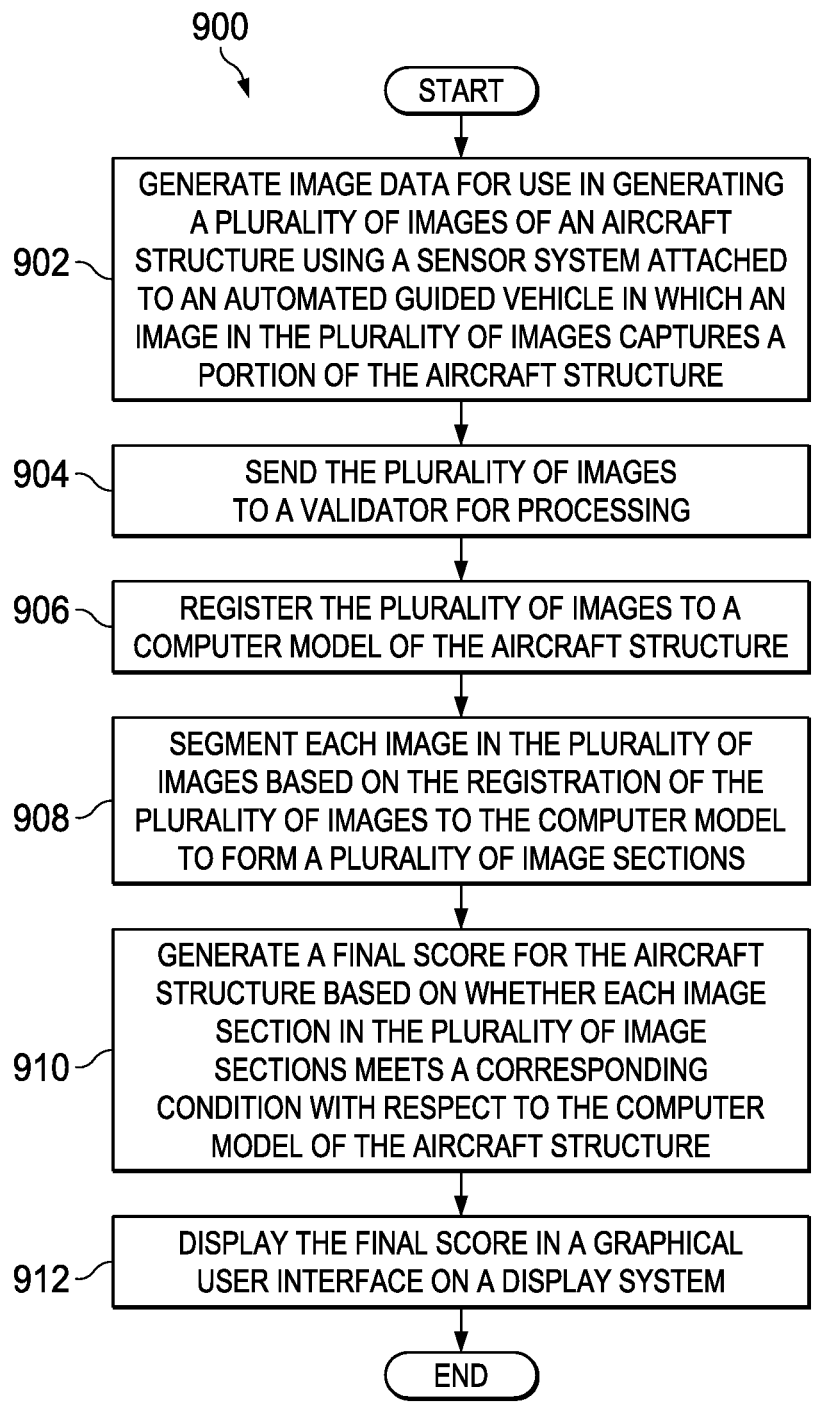
FIG. 9 is illustration of a method for performing an automated validation of a condition of assembly for an aircraft structure in accordance with an illustrative embodiment.

FIG. 9 is an illustration of a method for performing an automated validation of a condition of assembly for an aircraft structure, depicted in accordance with an illustrative embodiment. The method 900 illustrated in FIG. 9 may be used to perform, for example, automated validation process 202 as previously described in FIG. 2. The method 900 is illustrated as a set of operations or processes. Not all of the illustrated operations may be performed in all embodiments of method 900. Additionally, one or more processes that are not expressly illustrated in FIG. 9 may be included before, after, in between, or as part of the operations. In some embodiments, one or more of the operations may be optional and therefore omitted.

The method 900 may begin by generating image data for use in generating a plurality of images of an aircraft structure using a sensor system attached to an automated guided vehicle in which an image in the plurality of images captures a portion of the aircraft structure (operation 902). Next, the plurality of images are sent to a validator for processing (operation 904). The validator may be implemented using a processor or computer system. The plurality of images may be registered to a computer model of the aircraft structure (operation 906).

Thereafter, each image in the plurality of images may be segmented based on the registration of the plurality of images to the computer model to form a plurality of image sections (operation 908). A final score is generated for the aircraft structure based on whether each image section in the plurality of image sections meets a corresponding condition with respect to the computer model of the aircraft structure (operation 910). In operation 910, the final score indicates whether the condition of assembly for the structure is valid. The final score is then displayed in a graphical user interface on a display system (operation 912), with the process terminating thereafter.

Figure 10:
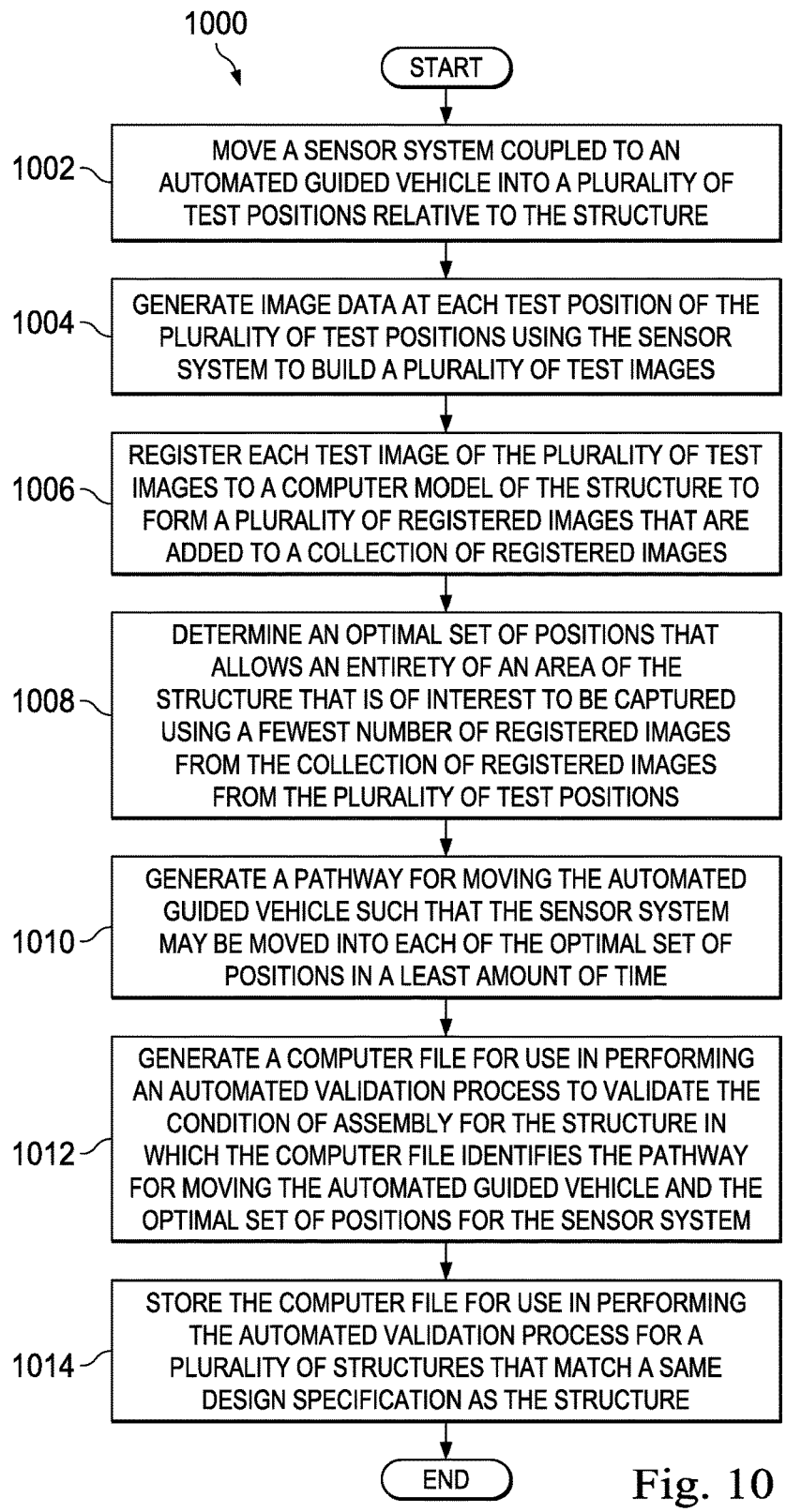
FIG. 10 is an illustration of a method for establishing a pathway for performing an automated validation process in accordance with an illustrative embodiment.

FIG. 10 is an illustration of a method for establishing a pathway for performing an automated validation process, depicted in accordance with an illustrative embodiment. The method 1000 illustrated in FIG. 10 may be used to establish a pathway, such as pathway 304 in FIG. 3, for performing automated validation process 202 as previously described in FIG. 2. The method 1000 is illustrated as a set of operations or processes. Not all of the illustrated operations may be performed in all embodiments of method 1000. Additionally, one or more processes that are not expressly illustrated in FIG. 10 may be included before, after, in between, or as part of the operations. In some embodiments, one or more of the operations may be optional and therefore omitted.

The method 1000 may begin by moving a sensor system coupled to an automated guided vehicle into a plurality of test positions relative to the structure (operation 1002). Operation 1002 may be performed by, for example, moving the automated guided vehicle along a predetermined test pathway to allow the sensor system to be moved into the plurality of test positions. Next, image data is generated at each test position of the plurality of test positions using the sensor system to build a plurality of test images (operation 1004). Each test image of the plurality of test images is registered to a computer model of the structure to form a plurality of registered images that are added to a collection of registered images (operation 1006).

Operation 1006 may be performed by, for example, without limitation, drawing correspondences between features of the structure that are detected in a test image and those same features in the computer model. This process may include using, for example, various algorithms and methodologies, including, but not limited to, RANSAC (the Random Sample Consensus algorithm) and ICP (the iterative closest point algorithm).

Thereafter, an optimal set of positions that allows an entirety of an area of the structure that is of interest to be captured using a fewest number of registered images from the collection of registered images is determined from the plurality of test positions (operation 1008). Next, a pathway is generated for moving the automated guided vehicle such that the sensor system may be moved into each of the optimal set of positions in a least amount of time (operation 1010). A computer file is generated for use in performing an automated validation process to validate the condition of assembly for the structure in which the computer file identifies the pathway for moving the automated guided vehicle and the optimal set of positions for the sensor system (operation 1012).

The computer file is then stored for use in performing the automated validation process for a plurality of structures that match a same design specification as the structure (operation 1014), with the process terminating thereafter. For example, the pathway and optimal set of positions identified in the computer file may be used to move the automated guided vehicle and sensor system, respectively, relative to other structures that are being assembled according to the same computer model as the structure for the purposes of performing the automated validation process. In some illustrative examples, the computer file may also be stored for use in performing the automated validation process for different assembly or stages of assembly or manufacturing for the structure.

Figure 11:
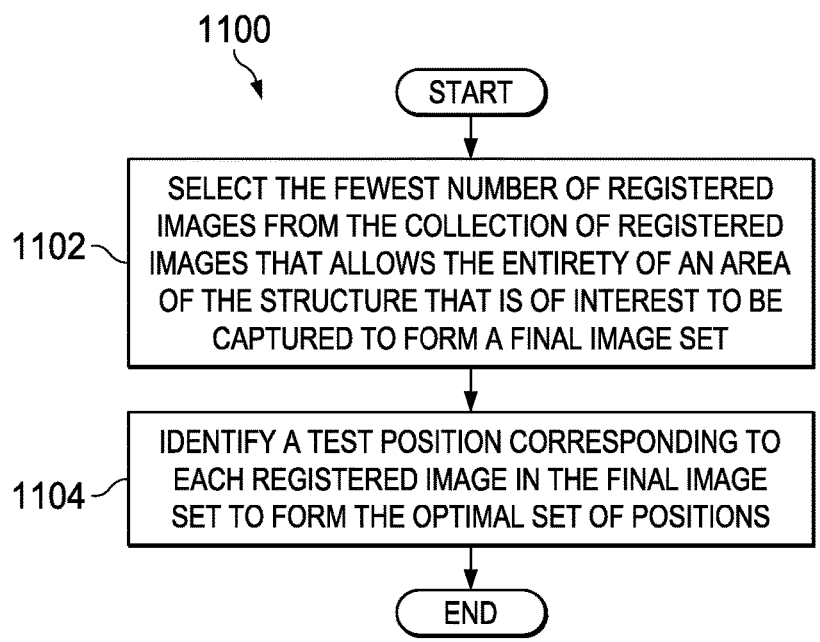
FIG. 11 is an illustration of a method for determining an optimal set of positions for performing an automated validation process in accordance with an illustrative embodiment.

FIG. 11 is an illustration of a method for determining an optimal set of positions for performing an automated validation process, depicted in accordance with an illustrative embodiment. The method 1100 illustrated in FIG. 11 may be an example of one process that may be used to implement operation 1008 in FIG. 10. The method 1100 is illustrated as a set of operations or processes. Not all of the illustrated operations may be performed in all embodiments of method 1100. Additionally, one or more processes that are not expressly illustrated in FIG. 11 may be included before, after, in between, or as part of the operations. In some embodiments, one or more of the operations may be optional and therefore omitted.

The method 1100 may begin by selecting the fewest number of registered images from the collection of registered images that allows the entirety of an area of the structure that is of interest to be captured to form a final image set (operation 1102). Next, a test position corresponding to each registered image in the final image set is identified to form the optimal set of positions (operation 1104), with the process terminating thereafter.

Figure 12:
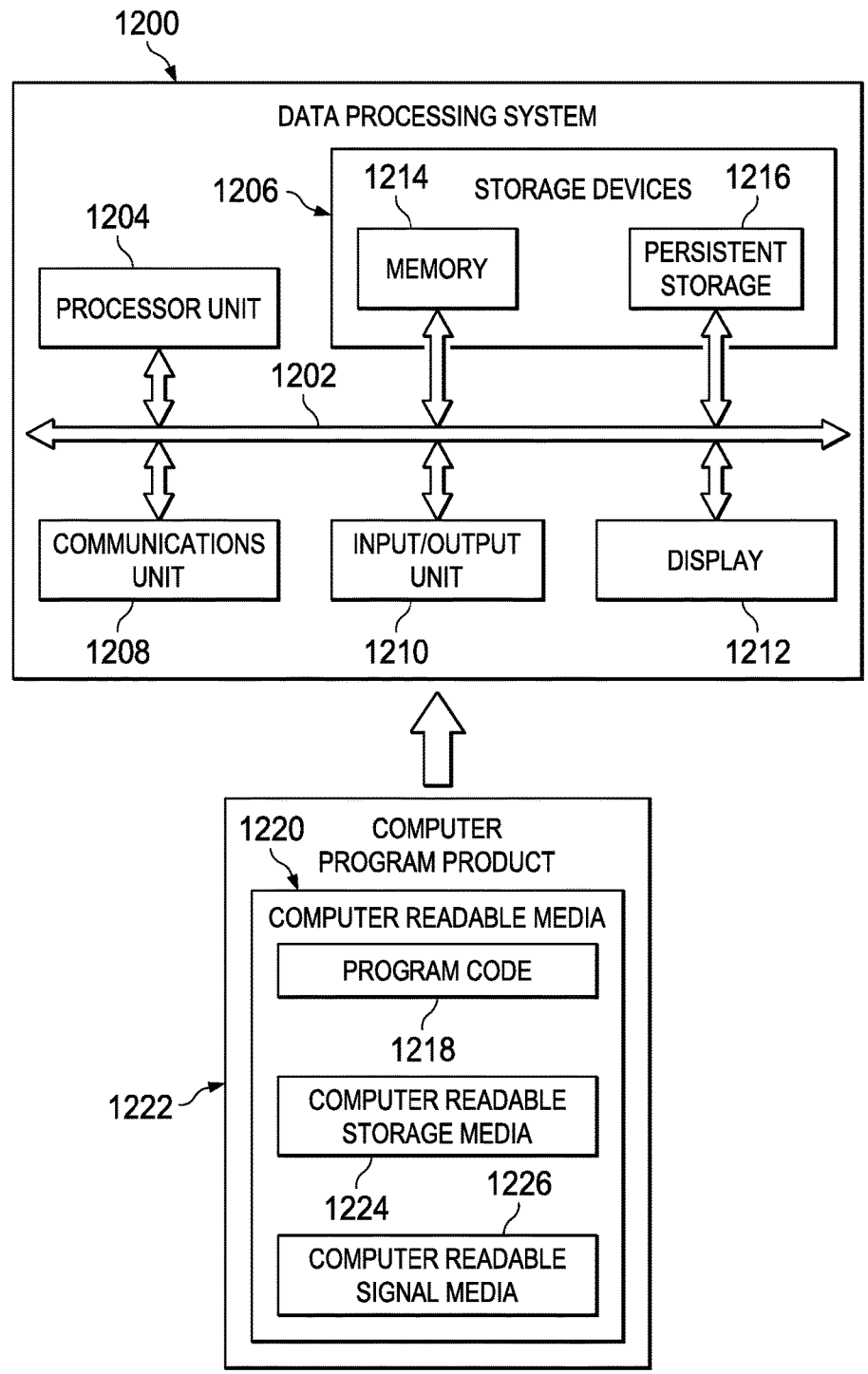
FIG. 12 is a block diagram of a data processing system in accordance with an illustrative embodiment.

FIG. 12 is a block diagram of a data processing system, depicted in accordance with an illustrative embodiment. Data processing system 1200 may be used to implement validator 212 in FIG. 1 and pathway generator 300 in FIG. 3. As depicted, data processing system 1200 includes communications framework 1202, which provides communications between processor unit 1204, storage devices 1206, communications unit 1208, input/output unit 1210, and display 1212. In some cases, communications framework 1202 may be implemented as a bus system.

Processor unit 1204 is configured to execute instructions for software to perform a number of operations. Processor unit 1204 may comprise a number of processors, a multiprocessor core, and/or some other type of processor, depending on the implementation. In some cases, processor unit 1204 may take the form of a hardware unit, such as a circuit system, an application specific integrated circuit (ASIC), a programmable logic device, or some other suitable type of hardware unit.

Instructions for the operating system, applications, and/or programs run by processor unit 1204 may be located in storage devices 1206. Storage devices 1206 may be in communication with processor unit 1204 through communications framework 1202. As used herein, a storage device, also referred to as a computer readable storage device, is any piece of hardware capable of storing information on a temporary and/or permanent basis. This information may include, but is not limited to, data, program code, and/or other information.

Memory 1214 and persistent storage 1216 are examples of storage devices 1206. Memory 1214 may take the form of, for example, a random access memory or some type of volatile or non-volatile storage device. Persistent storage 1216 may comprise any number of components or devices. For example, persistent storage 1216 may comprise a hard drive, a flash memory, a rewritable optical disk, a rewritable magnetic tape, or some combination of the above. The media used by persistent storage 1216 may or may not be removable.

Communications unit 1208 allows data processing system 1200 to communicate with other data processing systems and/or devices. Communications unit 1208 may provide communications using physical and/or wireless communications links.

Input/output unit 1210 allows input to be received from and output to be sent to other devices connected to data processing system 1200. For example, input/output unit 1210 may allow user input to be received through a keyboard, a mouse, and/or some other type of input device. As another example, input/output unit 1210 may allow output to be sent to a printer connected to data processing system 1200.

Display 1212 is configured to display information to a user. Display 1212 may comprise, for example, without limitation, a monitor, a touch screen, a laser display, a holographic display, a virtual display device, and/or some other type of display device.

In this illustrative example, the processes of the different illustrative embodiments may be performed by processor unit 1204 using computer-implemented instructions. These instructions may be referred to as program code, computer usable program code, or computer readable program code and may be read and executed by one or more processors in processor unit 1204.

In these examples, program code 1218 is located in a functional form on computer readable media 1220, which is selectively removable, and may be loaded onto or transferred to data processing system 1200 for execution by processor unit 1204. Program code 1218 and computer readable media 1220 together form computer program product 1222. In this illustrative example, computer readable media 1220 may be computer readable storage media 1224 or computer readable signal media 1226.

Computer readable storage media 1224 is a physical or tangible storage device used to store program code 1218 rather than a medium that propagates or transmits program code 1218. Computer readable storage media 1224 may be, for example, without limitation, an optical or magnetic disk or a persistent storage device that is connected to data processing system 1200.

Alternatively, program code 1218 may be transferred to data processing system 1200 using computer readable signal media 1226. Computer readable signal media 1226 may be, for example, a propagated data signal containing program code 1218. This data signal may be an electromagnetic signal, an optical signal, and/or some other type of signal that can be transmitted over physical and/or wireless communications links.

The illustration of data processing system 1200 in FIG. 12 is not meant to provide architectural limitations to the manner in which the illustrative embodiments may be implemented. The different illustrative embodiments may be implemented in a data processing system that includes components in addition to or in place of those illustrated for data processing system 1200. Further, components shown in FIG. 12 may be varied from the illustrative examples shown.

Figure 13:
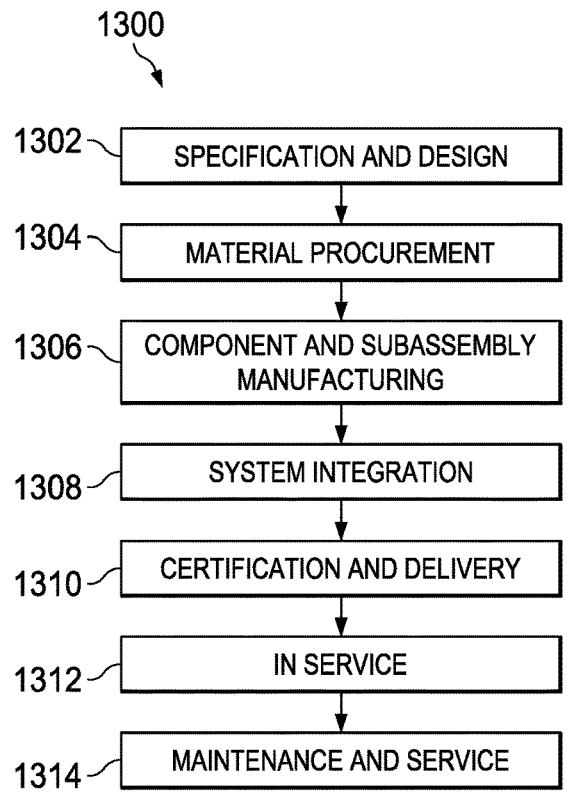
FIG. 13 is an illustration of an aircraft manufacturing and service method in accordance with an illustrative embodiment.
Figure 14:
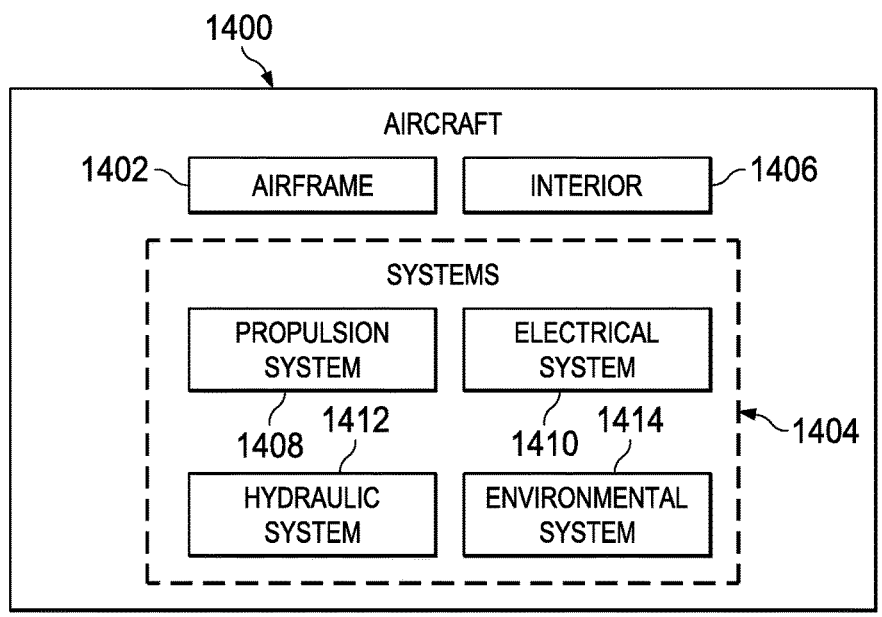
FIG. 14 is a block diagram of an aircraft in accordance with an illustrative embodiment.

Illustrative embodiments of the disclosure may be described in the context of aircraft manufacturing and service method 1300 as shown in FIG. 13 and aircraft 1400 as shown in FIG. 14. FIG. 13 is an illustration of an aircraft manufacturing and service method, depicted in accordance with an illustrative embodiment. Aircraft manufacturing and service method 1300 may be used to manufacture, for example, aircraft 100 in FIG. 1. During pre-production, aircraft manufacturing and service method 1300 may include specification and design 1302 of aircraft 1400 in FIG. 14 and material procurement 1304.

During production, component and subassembly manufacturing 1306 and system integration 1308 of aircraft 1400 in FIG. 14 takes place. Thereafter, aircraft 1400 in FIG. 14 may go through certification and delivery 1310 in order to be placed in service 1312. While in service 1312 by a customer, aircraft 1400 in FIG. 14 is scheduled for routine maintenance and service 1314, which may include modification, reconfiguration, refurbishment, and other maintenance or service.

Each of the processes of aircraft manufacturing and service method 1300 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

FIG. 14 is a block diagram of an aircraft, depicted in accordance with an illustrative embodiment. In this example, aircraft 1400 is produced by aircraft manufacturing and service method 1300 in FIG. 13 and may include airframe 1402 with plurality of systems 1404 and interior 1406. Examples of systems 1404 include one or more of propulsion system 1408, electrical system 1410, hydraulic system 1412, and environmental system 1414. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1300 in FIG. 13. In particular, automated validation process 202 from FIG. 2 may be performed during any one of the stages of aircraft manufacturing and service method 1300. For example, without limitation, validation system 208 in FIG. 2 may be used to perform automated validation process 202 to validate a condition of assembly for a structure of aircraft 1400 during at least one of component and subassembly manufacturing 1306, system integration 1308, routine maintenance and service 1314, or some other stage of aircraft manufacturing and service method 1300. Still further, pathway generator 300 from FIG. 3 may be used to establish a pathway for performing automated validation process 202 during any one of the stages of aircraft manufacturing and service method 1300.

In one illustrative example, components or subassemblies produced in component and subassembly manufacturing 1306 in FIG. 13 may be fabricated or manufactured in a manner similar to components or subassemblies produced while aircraft 1400 is in service 1312 in FIG. 13. As yet another example, one or more apparatus embodiments, method embodiments, or a combination thereof may be utilized during production stages, such as component and subassembly manufacturing 1306 and system integration 1308 in FIG. 13. One or more apparatus embodiments, method embodiments, or a combination thereof may be utilized while aircraft 1400 is in service 1312 and/or during maintenance and service 1314 in FIG. 13. The use of a number of the different illustrative embodiments may substantially expedite the assembly of and/or reduce the cost of aircraft 1400.

While certain exemplary embodiments of the invention have been described and shown in the accompanying drawings, it is to be understood that such embodiments are merely illustrative of and not restrictive on the broad invention. Additionally, it is to be understood that the embodiments of the invention are not be limited to the specific constructions and arrangements shown and described, since various other modifications may occur to those ordinarily skilled in the art.

Further, in the detailed description of the embodiments of the invention, numerous specific details have been set forth in order to provide a thorough understanding of the disclosed embodiments. However, it will be obvious to one skilled in the art that the embodiments of this disclosure may be practiced without these specific details. In some instances, well known methods, procedures, and components have not been described in detail so as not to unnecessarily obscure aspects of the embodiments of the invention.

What is claimed is:

1. A method of establishing a pathway for performing an automated validation of a condition of assembly for a structure, the method comprising:
    moving a sensor system coupled to an automated guided vehicle into a plurality of test positions relative to the structure;
    generating image data at each test position of the plurality of test positions using the sensor system to build a plurality of test images;
    registering each test image of the plurality of test images to a computer model of the structure to form a plurality of registered images that are added to a collection of registered images;
    determining an optimal set of positions from the plurality of test positions that allows an entirety of an area of the structure that is of interest to be captured using a fewest number of registered images from the collection of registered images;
    generating the pathway for moving the automated guided vehicle to each of the optimal set of positions in a least amount of time; and
    generating a computer file for use in performing an automated validation process to validate the condition of assembly for the structure in which the computer file identifies the pathway.

2. The method of claim 1, wherein moving the sensor system comprises:
    moving the automated guided vehicle along a straight-line path to allow the sensor system to be moved into the plurality of test positions.

3. The method of claim 1, wherein moving the sensor system comprises:
    moving the automated guided vehicle along a predetermined test pathway relative to the structure to allow the sensor system to be moved into the plurality of test positions.

4. The method of claim 1, wherein generating the image data at each test position comprises:
    generating a test image when the sensor system is moved into a test position, wherein the test position comprises a test location and a test orientation relative to a reference coordinate system.

5. The method of claim 1, wherein determining the optimal set of positions from the plurality of test positions comprises:
    selecting the fewest number of registered images from the collection of registered images that allows the entirety of the area of the structure that is of interest to be captured to form a final image set; and
    identifying a test position corresponding to each registered image in the final image set to form the optimal set of positions.

6. The method of claim 5, wherein identifying the test position corresponding to each registered image comprises:
    identifying a test location and a test orientation for the sensor system corresponding to a registered image in the final image set.

7. The method of claim 1, wherein moving the sensor system comprises:
    moving the sensor system to between about 100 and about 100,000 test positions relative to the structure, wherein each test position comprises a test location and a test orientation relative to a reference coordinate system.

8. The method of claim 1 further comprising:
    moving the sensor system coupled to the automated guided vehicle into the optimal set of positions along the pathway identified in the computer file to perform the automated validation process.

9. The method of claim 1 further comprising:
    storing the computer file for use in performing the automated validation process for a plurality of structures that match a same design specification as the structure.

10. The method of claim 1, wherein performing the automated validation process using the computer file reduces an overall amount of processing resources needed to perform the automated validation of the condition of assembly.

11. A method of establishing a pathway for performing an automated validation of a condition of assembly for a fuselage structure, the method comprising:
    moving a sensor system coupled to an automated guided vehicle into a plurality of test positions through the fuselage structure;
    generating image data at each test position of the plurality of test positions using the sensor system to build a plurality of test images;
    registering each test image of the plurality of test images generated to a computer model of the fuselage structure;
    determining an optimal set of positions from the plurality of test positions that allows an entirety of an area of the fuselage structure that is of interest to be captured using a fewest number of test images;
    generating a pathway for moving the automated guided vehicle to each of the optimal set of positions in a least amount of time; and
    generating a file for use in performing an automated validation process to validate the condition of assembly for the fuselage structure in which the file identifies the pathway.

12. The method of claim 11, wherein moving the sensor system comprises:
    moving the automated guided vehicle along a straight-line path along a centerline through the fuselage structure.

13. The method of claim 11, wherein generating the image data comprises:
generating a test image at a test position, wherein the test image captures at least one of a plurality of holes in the fuselage structure or a plurality of fasteners installed in the plurality of holes in the fuselage structure.

14. The method of claim 11 further comprising:
storing the computer file for use in performing the automated validation process for a plurality of fuselage structures that match a same design specification as the fuselage structure.

15. The method of claim 11 further comprising:
storing the computer file for use in performing the automated validation process for different stages of assembly for the fuselage structure.

16. An apparatus comprising:
a processor that comprises:
a registration component that receives a plurality of test images from a sensor system that generated the plurality of test images at a plurality of test positions relative to a structure and registers each test image of the plurality of test images generated to a computer model of the structure; and
an optimizing component that determines an optimal set of positions from the plurality of test positions that allows an entirety of an area of the structure that is of interest to be captured using a fewest number of test images; generates a pathway for moving an automated guided vehicle to each of the optimal set of positions in a least amount of time; and generates a file for use in performing an automated validation of a condition of assembly for the structure in which the file identifies the pathway.

17. The apparatus of claim 16 further comprising:
the sensor system, wherein the sensor system is coupled to an automated guided vehicle configured to move the sensor system into the plurality of test positions relative to the structure.

18. The apparatus of claim 16, wherein the structure is a fuselage structure and wherein a test image in the plurality of test images captures at least one of a plurality of holes in the fuselage structure or a plurality of fasteners installed in the plurality of holes in the fuselage structure.

19. The apparatus of claim 16, wherein the plurality of test images includes between about 100 and 100,000 test images.

20. The apparatus of claim 16, wherein a test image in the plurality of test images generated at a test position corresponds to a particular test location and a particular test orientation for the sensor system with respect to a reference coordinate system.

* * * * *